(12) United States Patent
Long et al.

(10) Patent No.: US 9,943,572 B2
(45) Date of Patent: Apr. 17, 2018

(54) SYNERGISTIC GLYCOCALYX TREATMENT COMPOSITIONS AND METHODS

(71) Applicant: Microvascular Health Solutions, LLC, Alpine, UT (US)

(72) Inventors: Robert Maxfield Long, Alpine, UT (US); Hans Vink, Schimmert (NL)

(73) Assignee: Microvascular Health Solutions, LLC, Alpine, UT (US)

( * ) Notice: Subject to any disclaimer, the term of this patent is extended or adjusted under 35 U.S.C. 154(b) by 119 days.

(21) Appl. No.: 15/094,757

(22) Filed: Apr. 8, 2016

(65) Prior Publication Data

US 2016/0296603 A1    Oct. 13, 2016

Related U.S. Application Data

(60) Provisional application No. 62/144,484, filed on Apr. 8, 2015.

(51) Int. Cl.

| | |
|---|---|
| A61K 38/44 | (2006.01) |
| A61K 31/7008 | (2006.01) |
| A61K 31/728 | (2006.01) |
| A61K 31/737 | (2006.01) |
| A61K 31/05 | (2006.01) |
| A61K 35/744 | (2015.01) |
| A61K 36/03 | (2006.01) |

(52) U.S. Cl.
CPC ............ *A61K 38/446* (2013.01); *A61K 31/05* (2013.01); *A61K 31/7008* (2013.01); *A61K 31/728* (2013.01); *A61K 31/737* (2013.01); *A61K 35/744* (2013.01); *A61K 36/03* (2013.01); *C12Y 111/01006* (2013.01); *C12Y 115/01001* (2013.01)

(58) Field of Classification Search
None
See application file for complete search history.

(56) References Cited

U.S. PATENT DOCUMENTS

| | | |
|---|---|---|
| 6,797,705 B2 | 9/2004 | Daniels |
| 7,214,666 B1 | 5/2007 | Madere |
| 2007/0141181 A1 | 6/2007 | Henderson et al. |
| 2011/0183006 A1 | 7/2011 | Yamka et al. |
| 2013/0273096 A1 | 10/2013 | Daniels |
| 2014/0323432 A1 | 10/2014 | Minami et al. |

FOREIGN PATENT DOCUMENTS

| | | | |
|---|---|---|---|
| WO | WO 2009/121959 | * | 10/2009 |
| WO | WO 2009-121959 | | 10/2009 |

OTHER PUBLICATIONS

International Search Report and Written Opinion dated Sep. 27, 2016, Application No. PCT/US2016/026739, filed Apr. 8, 2016.
Charmaine B. S. Henry et al., *Permeation of the Luminal Capillary Glycocalyx is Determined by Hyaluronan*, http://ajpheart.physiology.org/ by 10.220.33.5, Oct. 31, 2016, pp. H508-H514.
Lajos Balogh et al., *Absorption, Uptake and Tissue Affinity of High-Molecular-Weight Hyaluronan after Oral Administration in Rats and Dogs*, J. Agric. Food Chem., 2008, vol. 56, pp. 10582-10593.

* cited by examiner

*Primary Examiner* — Thane Underdahl
(74) *Attorney, Agent, or Firm* — Workman Nydegger

(57) ABSTRACT

Compositions and methods for treating endothelial glycocalyx include glucosamine, hyaluronan and/or fucoidan, and one or more antioxidants, such as superoxide dismutase, catalase, and/or polyphenol. The compositions improve vascular health by exhibiting beneficial synergistic effects on endothelial glycocalyx over the benefits of taking any single component alone or the sum of reported effects of the individual components. Specifically, components of the composition (1) enhance synthesis of new glycocalyx by (a) providing and (b) increasing production of glycocalyx precursors, (2) protecting existing glycocalyx against damage, such as by oxidation degradation, by (a) providing and (b) increasing production of antioxidants, some of which associate with endothelial glycocalyx, and (3) enhance repair of damaged glycocalyx by (a) providing glycocalyx mimetics and (b) increasing the prevalence of glycocalyx scaffold for association and incorporation thereof.

19 Claims, 5 Drawing Sheets

SYNERGISTIC GLYCOCALYX TREATMENT COMPOSITIONS AND METHODS

CROSS-REFERENCE TO RELATED APPLICATIONS

The present application claim the benefit of priority to U.S. Provisional Application No. 62/144,484, filed on Apr. 8, 2015, entitled "SYNERGISTIC GLUCOSAMINE COMPOSITIONS AND USES," the entire contents of which is incorporated herein by specific reference.

BACKGROUND

1. Technical Field

The present disclosure relates to compositions and methods for improving vascular health. Specifically, the present disclosure relates to synergistic compositions and methods of treating endothelial glycocalyx.

2. Relevant Technology

The glycocalyx is a polysaccharide-rich layer found on the luminal surface of epithelial cells lining mammalian organs and tissues. In the case of the vascular system, the glycocalyx coats the luminal surface of the endothelium—the vascular endothelial cells lining the inside of all blood vessels. As depicted in FIG. 1, for example, in vivo imaging of a capillary blood vessel illustrates that red blood cells (RBC) flowing through the lumen of the blood vessel do not contact the vessel wall endothelium. FIG. 2 illustrates a detailed view of an electron micrograph image capturing a cross-section of a capillary. As depicted, the dense glycocalyx extends from the endothelial cells into the lumen of the blood vessel, forming a micro-thin, gel-like layer.

Until recently, the role of the endothelial glycocalyx had not been well understood. In theory, however, the glycocalyx may act as a protective barrier for the vascular wall or may provide a micro-environment for certain vascular processes. Molecules that associate with the glycocalyx may dynamically interact with the endothelial cells to play a role in orchestrating a variety of functions in the circulatory system. The circulatory system, in turn, plays a role in regulating adequate organ perfusion and in the distribution and exchange of oxygen, nutrients, and hormones within tissues. Furthermore, microcirculation controls tissue hydration and organizes the defense against pathogens.

As illustrated in FIGS. 2A-2D, endothelial glycocalyx can be observed in varying degrees of thickness and/or density; indications of the "health" of the endothelial glycocalyx. FIG. 2A, for example, depicts an electron micrograph image of a "healthy" endothelial glycocalyx, while FIG. 2D depicts a severely damaged or perturbed "unhealthy" endothelial glycocalyx. FIG. 2B and FIG. 2C illustrate, respectively, intermediate states of endothelial glycocalyx health (e.g., as indicated visually by the thickness and/or density thereof). The cause(s) of such structural damage and/or depletion of the endothelial glycocalyx remain largely unknown.

Impairment of the glycocalyx barrier through structural damage or depletion, functional deficiency, or other mechanism may be a contributing cause of microvascular endothelial dysfunction, including inflammatory and coagulatory endothelial activation, vascular leakage of fluid, proteins, and other substances (e.g., cholesterol), failure to properly modulate perfused blood vessel density, and other deleterious conditions, leading to general and specific negative vascular health indicators. As depicted in FIG. 3B, for example, an unhealthy endothelial glycocalyx is associated with a "leaky" endothelium, as evidenced by (1) the presence (or "leakage") of cholesterol (or other substances, such as fluids, proteins, etc.) in (or into) the subendothelial space, and (2) a constricted lumen, which may reduce blood flow or perfusion into distal capillaries, muscles, organs, etc., increase blood pressure, and so forth. As illustrated in FIG. 3A, however, a healthy (thick and/or dense) endothelial glycocalyx is associated with a well-formed endothelium and healthy blood vessel structural configuration.

Accordingly, there is a need for products and processes for treating (e.g., supporting and/or maintaining) endothelial glycocalyx.

BRIEF SUMMARY

Embodiments of the present disclosure address one or more of the foregoing or other problems in the art with compositions and methods for treating endothelial glycocalyx. The compositions can include nutritional building blocks required to support and maintain a healthy endothelial glycocalyx, antioxidants to help prevent damage to the glycocalyx, and/or glycocalyx mimetics for acute repair of damaged endothelial glycocalyx. In at least one embodiment, the building blocks comprise glucosamine, the antioxidants comprise superoxide dismutase, catalase, and/or one or more polyphenols, and the glycocalyx mimetics comprise hyaluronan and/or fucoidan. The components can be combined in an orally administrable form.

The components of the compositions can act synergistically to improve vascular health by supporting a healthy endothelial glycocalyx. In other words, the combination of components included in the compositions can provide an effect on glycocalyx maintenance that is greater than taking any single component alone or the sum of reported effects of the individual components. For instance, the nutritional building blocks can aid not only in the synthesis of new glycocalyx, but also in acute repair of damaged glycocalyx and/or protecting the glycocalyx against structural damage. Similarly, the antioxidants can not only help to prevent damage to the glycocalyx, but also aid in acute repair of damaged glycocalyx and/or synthesis of new glycocalyx. Likewise, the glycocalyx mimetics can not only induce acute repair of damaged glycocalyx, but also aid in the synthesis of new glycocalyx and/or help to prevent damage to the glycocalyx.

An embodiment of the present disclosure can include a composition for treating endothelial glycocalyx, the composition comprising glucosamine, hyaluronan and/or fucoidan, and one or more antioxidants, such as superoxide dismutase, catalase, and/or polyphenol. The composition can exhibit a synergistic, therapeutic effect on the endothelial glycocalyx when administered to a mammal.

Another aspect of the present disclosure includes repairing damaged endothelial glycocalyx by providing and/or administering exogenous (nonsulfated) glycosaminoglycan and/or (sulfated) polysaccharides, such as hyaluronan and/or fucoidan, that associate with existing glycocalyx structures at sites of glycocalyx perturbation.

A further aspect of the present disclosure includes stimulating endothelial glycocalyx synthesis by providing and/or administering glycocalyx precursor and/or substrate, such as glucosamine, for local production and incorporation of glycocalyx constituents.

Yet another aspect of the present disclosure includes reducing damage (e.g., (oxidative) degradation) of endothelial glycocalyx and/or constituents thereof by providing antioxidant enzymes, such as superoxide dismutase and/or catalase, and/or antioxidant compounds, such as polyphenols, that reduce (excessive, local) levels or concentrations of reactive oxygen species.

Additional features, aspects, and advantages of exemplary embodiments of the present disclosure will be set forth in the description which follows and, in part, will be apparent from the description or may be learned by the practice of such exemplary embodiments. The features and advantages of such embodiments may be realized and obtained by means of the instruments and combinations particularly pointed out in the appended claims. These and other features, aspects, and advantages will become more fully apparent to those of skill in the art from the following description and appended claims, or may be learned by the practice of such exemplary embodiments as set forth hereinafter.

BRIEF DESCRIPTION OF THE DRAWINGS

In order to describe the manner in which the above-recited and other advantages and features of the present disclosure can be obtained, a more particular description of various embodiments of the present disclosure will now be rendered with reference to the appended drawings, in which the exemplary embodiments are illustrated. It is appreciated that these drawings depict only typical embodiments of the present disclosure and are not, therefore, to be considered limiting of its scope.

DETAILED DESCRIPTION

Figure 1A:
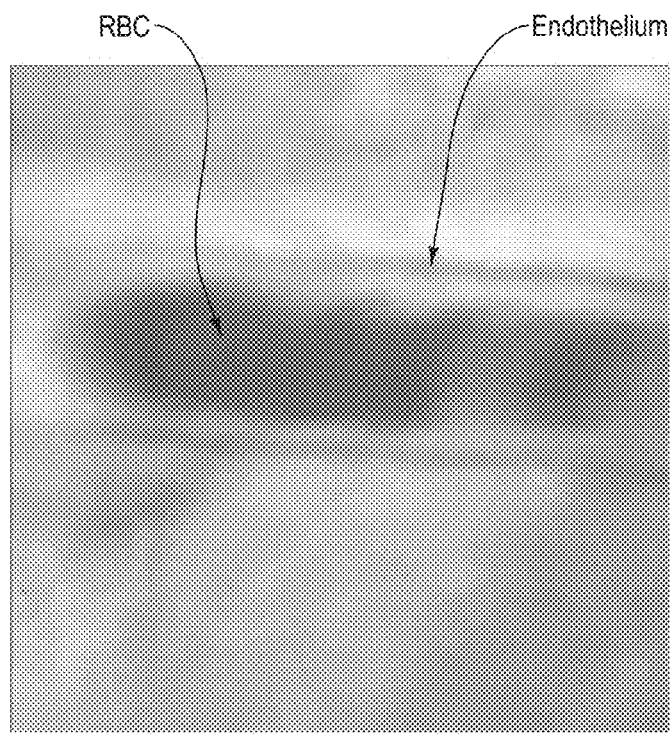
FIG. 1A is an in vivo image of a capillary blood vessel.
Figure 1B:
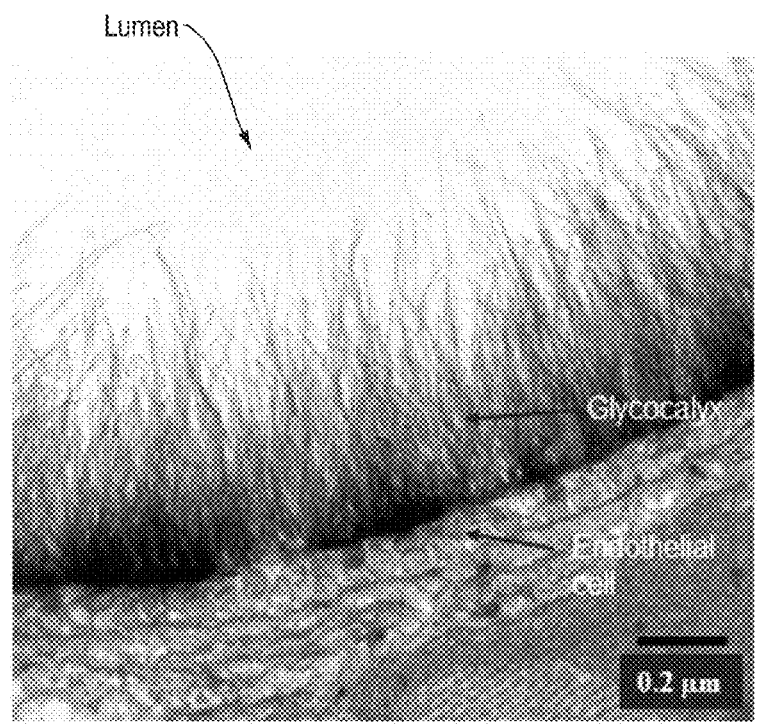
FIG. 1B is a detailed view of an electron micrograph image capturing a cross-section of a capillary blood vessel.
Figures 2A, 2B, 2C, 2D:
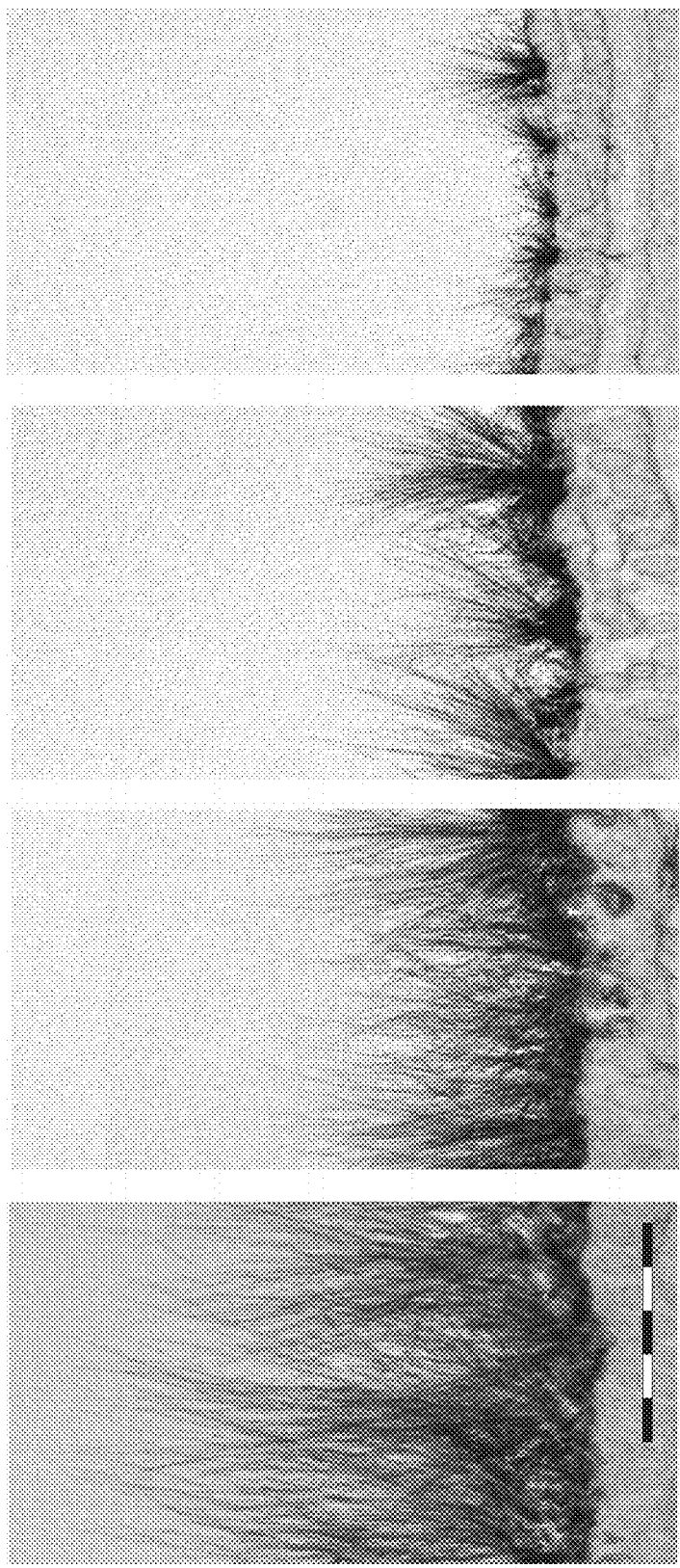
FIGS. 2A-2D illustrate diminishing health of endothelial glycocalyx.
Figure 3A:
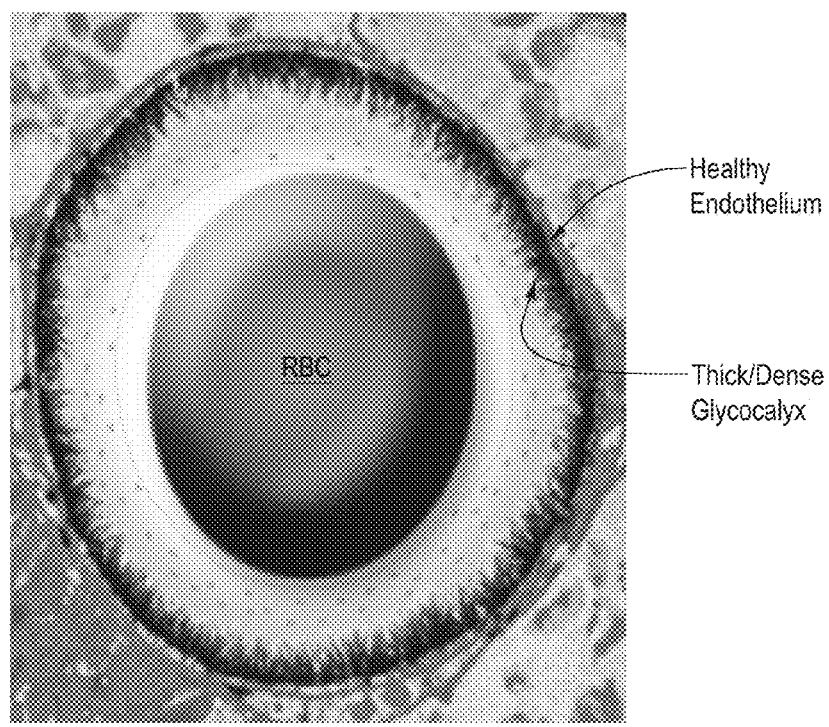
FIG. 3A illustrates an electron micrograph image capturing a cross-section of a blood vessel having a generally healthy glycocalyx.
Figure 3B:
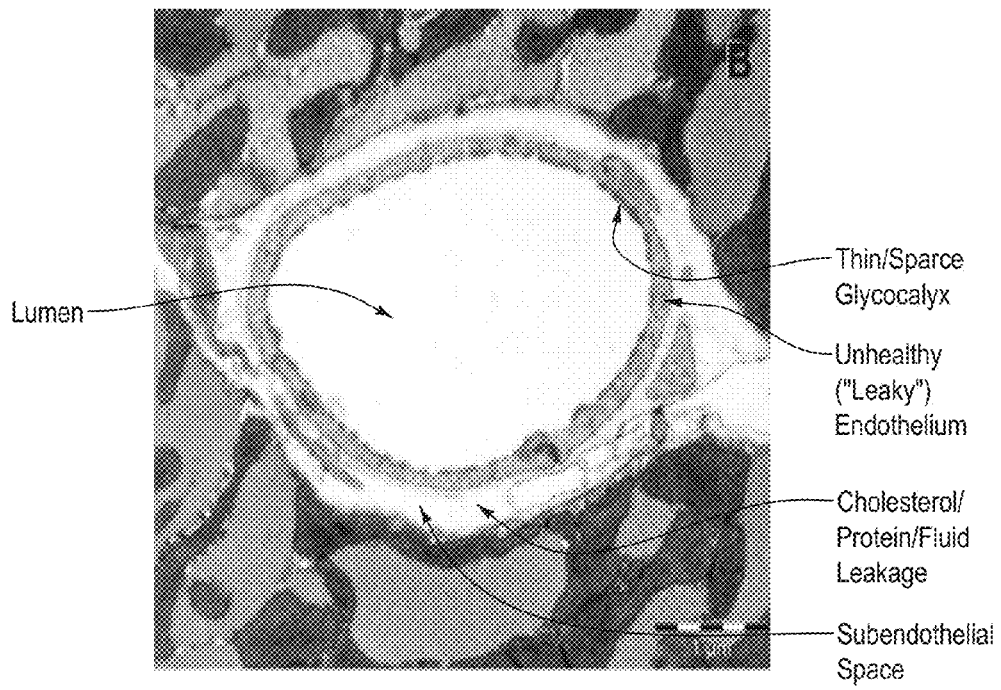
FIG. 3B illustrates an electron micrograph image capturing a cross-section of a blood vessel having a generally unhealthy glycocalyx.

Before describing the present disclosure in further detail, it is to be understood that this disclosure is not limited to the description of the particularly exemplified methods and/or products that may vary from one embodiment to the next. Thus, while certain embodiments of the present disclosure will be described in detail, with reference to specific configurations, parameters, features (e.g., components, members, elements, parts, and/or portions), etc., the descriptions are illustrative and are not to be construed as limiting the scope of the claimed invention. In addition, the terminology used herein is for the purpose of describing the embodiments, and is not necessarily intended to limit the scope of the claimed invention.

Unless defined otherwise, all technical and scientific terms used herein have the same meaning as commonly understood by one of ordinary skill in the art to which the present disclosure pertains.

Various aspects of the present disclosure, including systems, processes, and/or products may be illustrated with reference to one or more implementations or embodiments, which are exemplary in nature. As used herein, the terms "embodiment" and "implementation" mean serving as an example, instance, or illustration, and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be noted that, as used in this specification and the appended claims, the singular forms "a," "an" and "the" include plural referents unless the context clearly dictates otherwise. Thus, for example, reference to a "polyphenol" includes one, two, or more polyphenols. Similarly, plural referents, such as "polyphenols," should be interpreted as comprising a single referent and/or a plurality of referents unless the content and/or context clearly dictate otherwise. Thus, reference to "polyphenols" does not necessarily require a plurality of such polyphenols. Instead, it will be appreciated that independent of conjugation; one or more polyphenols are contemplated herein.

To facilitate understanding, like references (i.e., like naming of components and/or elements) have been used, where possible, to designate like elements common to the description and/or figures. Specifically, in the exemplary embodiments described herein and/or illustrated in the figures, like structures, or structures with like functions, may be provided with similar names and/or reference designations, where possible. Specific language will be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential).

It will also be appreciated that where multiple possibilities of values or a range of values (e.g., less than, greater than, at least, and/or up to a certain value, and/or between two recited values) is disclosed or recited, any specific value or range of values falling within the disclosed range of values is likewise disclosed and contemplated herein. Thus, disclosure of an illustrative measurement or amount less than or equal to about 10 units or between 0 and 10 units includes, illustratively, a specific disclosure of: (i) a measurement or amount of 9 units, 5 units, 1 units, or any other value between 0 and 10 units, including 0 units and/or 10 units; and/or (ii) a measurement or amount between 9 units and 1 units, between 8 units and 2 units, between 6 units and 4 units, and/or any other range of values between 0 and 10 units.

Weight—or mass-based measurements provided herein (e.g., milligrams (mg)) are given on a dry weight or dry mass basis.

The headings used herein are for organizational purposes only and are not meant to be used to limit the scope of the description or the claims.

Embodiments of the present disclosure address and/or provide solutions to the problem of glycocalyx deficiency, dysfunction, degradation, vascular health-related problems resulting therefrom, and/or one or more of the foregoing or other problems in the art with novel, effective, and/or synergistic compositions and methods for treating endothelial glycocalyx. As used herein the term "synergistic" refers to the phenomenon where the combination of two or more components (e.g., therapeutic agents, ingredients, etc.) provides an effect that is greater than the effect of the individual components or the sum of the components acting alone. Thus, embodiments of the present disclosure can include a combination or mixture of components in an amount effective to produce or exhibit a (physiological) effect (when administered to a subject or patient in need thereof) that is greater than the effect of any single component or the sum of the effects of each component acting alone.

Some embodiments can include one or more nutritional building blocks (e.g., glycocalyx precursor or substrate molecule) adapted to support and maintain a healthy endothelial glycocalyx (e.g., by increasing (natural) production thereof). Such glycocalyx building blocks, precursors, and/or substrate molecules can include, for example, glucosamine (e.g., glucosamine sulfate). Some embodiments can include one or more antioxidant (e.g., enzyme or compound) to help prevent damage to the glycocalyx. Such antioxidant can include, for example, superoxide dismutase (SOD) (e.g., extracellular SOD, SOD3, copper- or zinc-conjugated SOD, etc.), catalase (e.g., iron(III)- or iron(IV)-conjugated catalase), and/or one or more polyphenols. Some embodiments can include one or more glycocalyx mimetics, glycocalyx-binding compound, or glycocalyx-associating compounds for acute repair of damaged glycocalyx or sites of glycocalyx damage (e.g., degradation, alteration, thinning, etc.). Such glycocalyx mimetics, glycocalyx-binding compound, or glycocalyx-associating compounds can include, for example, hyaluronan (e.g., sodium hyaluronate) and/or fucoidan (e.g., fucoidan sulfate). The components of the compositions can act synergistically to improve vascular health by supporting a healthy endothelial glycocalyx, such that the combination of components can provide an effect on glycocalyx maintenance that is greater than taking any single component alone or the sum of reported effects of the individual components. In at least one embodiment, a composition for use in treating endothelial glycocalyx is provided.

Some embodiments of the present disclosure include one or more methods of (synergistically) treating (e.g., supporting, maintaining, protecting, repairing, patching, and/or enhancing production of) endothelial glycocalyx, methods of improving vascular health, methods of restoring healthy endothelial glycocalyx, etc. Embodiments can also achieve a desired result (e.g., physiological reaction, biological response, etc.), such as increased endothelial glycocalyx density or thickness, reduced endothelial glycocalyx damage or degradation, improved vascular shear stress signaling, reduced blood pressure, increased blood nitric oxide levels and/or production, increased oxygen exchange, decreased endothelial permeability (e.g., to large plasma molecules, thereby decreasing leakage thereof into or across the endothelium), reduced accumulation of cholesterol in subendothelial space, increased size or volume of perfused boundary region, improved blood perfusion or distribution (e.g., to capillaries, organs, muscles, etc.), microvascular blood volume, and so forth.

Embodiments can include providing or administering to a subject or patient (e.g., mammal, human, etc.) an effective amount of a composition, or a composition in an amount effective, to (synergistically) treat endothelial glycocalyx, improve vascular health, restore healthy endothelial glycocalyx, etc. The composition can include an effective amount of one or more nutritional building blocks that can aid not only in the synthesis of new glycocalyx, but also in acute repair of damaged glycocalyx and/or protecting the glycocalyx against structural damage. The composition can also include an effective amount of one or more antioxidants that can not only help to prevent damage to the glycocalyx, but also aid in acute repair of damaged glycocalyx and/or synthesis of new glycocalyx. The composition can also include an effective amount of one or more glycocalyx mimetics that can not only induce acute repair of damaged glycocalyx, but also aid in the synthesis of new glycocalyx and/or help to prevent damage to the glycocalyx.

By repairing, protecting, and enhancing synthesis of endothelial glycocalyx, embodiments of the present disclosure can treat (e.g., bolster, maintain, support, etc.) the glycocalyx, (e.g., ensuring structural and functional integrity thereof). Such structural and functional integrity can be associated with overall vascular (e.g., microvascular) health and function, including proper regulation and/or modulation of perfused blood vessel density, blood pressure, vascular barrier properties, blood flow or perfusion into distal capillaries, muscles, organs, etc., inflammatory and/or coagulatory response, and so forth.

Illustrative components (and combinations thereof) useful in the formation, production, and/or manufacture of certain embodiments of the present disclosure, and illustrative methods (and steps thereof) involving the same, will be discussed in further detail below. For organizational purposes only, such components have been grouped into three categories based on their direct and/or primary function or mode of action in treating (e.g., supporting or maintaining) a (healthy) endothelial glycocalyx. Such modes of actions include (1) synthesizing (or producing new) endothelial glycocalyx (e.g., through supporting natural pathways and/or processes with glycocalyx precursors or building blocks), (2) repairing (or patching) damaged or perturbed glycocalyx (structural features) (e.g., with glycocalyx-mimetics), and (3) protecting (or defending) existing endothelial glycocalyx (e.g., with antioxidants).

1. Synthesizing Endothelial Glycocalyx—Glycocalyx Precursors

Glucosamine

Glucosamine is an amino sugar and a precursor in the biochemical synthesis of glycosylated proteins and lipids. Although there is a substantial amount of data about the health benefits of glucosamine, its exact role in glycocalyx synthesis has not been previously recognized or documented. For example, it has not been reported or recognized that (soluble and/or exogenous) glucosamine (e.g., glucosamine sulfate) can be introduced (orally, intravenously, etc.) to stimulate synthesis of endothelial glycocalyx (through natural biochemical pathways), as contemplated by the present disclosure.

Indeed, glucosamine can increase synthesis of two main constituents of the endothelial glycocalyx, namely heparan sulfate and hyaluronan. Moreover, labeled glucosamine administered to cultured endothelial cells is incorporated in the glycocalyx. Thus, the addition and/or administration of glucosamine can support endothelial glycocalyx production by providing a (necessary and/or rate-limiting) component in the synthesis thereof. Accordingly, glucosamine can be or comprise a molecular precursor of endothelial glycocalyx.

One or more embodiments of the present disclosure can include glucosamine (e.g., in an amount effective to increase vascular production of endothelial glycocalyx). In some embodiments the glucosamine can be included (or provided) as glucosamine sulfate and/or other form of (D-)glucosamine. The glucosamine can be natural or synthetic. In a preferred embodiment, the glucosamine can be or comprise glucosamine (sulfate) extracted and/or purified from a (non-GMO) plant source, such as vegetable(s), (e.g., corn). In at least one embodiment, the glucosamine (sulfate) (extract) can have a purity greater than or equal to about 80%, 85%, 90%, 95%, 96%, 97%, 98%, or 99%.

The glucosamine can be included in compositions of the present disclosure in an amount of at least about 50 mg, 100 mg, 200 mg, 250 mg, 300 mg, 350 mg, 375 mg, 400 mg, 500 mg, 600 mg, 700 mg, 750 mg, 800 mg, 900 mg, 1000 mg, 1200 mg, 1500 mg, 2000 mg, 2500 mg, 3000 mg, or more. In a preferred embodiment, glucosamine can be provided in an amount sufficient to result in the administration of about 1500 mg of glucosamine (or glucosamine extract) per day. per day. Accordingly, certain embodiments (e.g., a daily dose) can include about 1500 mg of (corn) glucosamine (sulfate) (extract).

2. Repairing Endothelial Glycocalyx—Glycocalyx-Mimetics

Hyaluronan

Hyaluronan, or hyaluronic acid, is a polysaccharide with a structure similar to heparan sulfate and heparin; that is, it includes repeats of the monosaccharides glucosamine and glucuronic acid. Unlike heparan sulfate, however, hyaluronan is a nonsulfated glycosaminoglycan (that lacks sulfation) and is not linked to a core protein. Endogenous hyaluronan also associates with the glycocalyx, becoming incorporated into the endothelial membrane by its synthesizing enzyme hyaluronan synthase ("HAS") or via binding to CD44 or other hyaluronan binding proteins.

Although reports of some of the benefits of hyaluronan are known, especially in patients with fibromyalgia, it has not been previously recognized that hyaluronan is a part of glycocalyx repair. In particular, although hyaluronan is a building block of the glycocalyx, it has not been previously known or recognized that hyaluronan can be introduced to repair damaged glycocalyx (at sites of glycocalyx damage or perturbation), as contemplated by the present disclosure. Furthermore, due to its high molecular weight (e.g., reaching long lengths of up to several microns), it is also unclear to what degree (orally) administered (exogenous) hyaluronan can or does enter the circulatory system (e.g., by means of the lymphatic system) intact. For instance, without being bound to any theory, the half-life of hyaluronan in the circulatory system may be very short (e.g., 5 minutes or less). While existing theory and/or accepted wisdom attributes the short half-life of hyaluronan to enzymatic or other degradation (e.g., by oxidants, such as free radicals), the present disclosure reports the (direct) association of hyaluronan with and/or binding of hyaluronan to existing endothelial glycocalyx (e.g., resulting in the rapid decrease of free, circulating hyaluronan after administration).

Indeed, hyaluronan can be, act as, and/or provide a glycocalyx-mimetic (or patch) that associates with existing glycocalyx structures at sites of glycocalyx perturbation. Introduction and/or administration of (exogenous) hyaluronan causes thickening of endothelial glycocalyx at sites of damage and/or thinning of the glycocalyx. Thus, in addition to (naturally) produced hyaluronan, which is synthesized and incorporated into the endothelium, exogenous or administered hyaluronan can (directly) associate with existing glycocalyx and/or glycocalyx-sparse regions of the endothelium.

One or more embodiments of the present disclosure can include hyaluronan (e.g., in an amount effective to increase the density of endothelial glycocalyx). In some embodiments the hyaluronan can be included (or provided) as sodium hyaluronate. The hyaluronan can be natural or synthetic. In a preferred embodiment, the hyaluronan can be or comprise hyaluronan (sodium salt) extracted and/or purified from a (non-GMO) microbial (e.g., bacterial) source, such as *Streptoccoccus*, (e.g., *Streptoccoccus equi* subsp. *Zooepidemicus*). In at least one embodiment, the hyaluronan (sodium salt) (extract) can have a purity greater than or equal to about 80%, 85%, 90%, 92%, 95%, 96%, 97%, 98%, or 99%.

The hyaluronan can be included in compositions of the present disclosure in an amount of at least about 5 mg, 10 mg, 12 mg, 15 mg, 17.5 mg, 20 mg, 25 mg, 30 mg, 35 mg, 40 mg, 50 mg, 60 mg, 70 mg, 75 mg, 80 mg, 90 mg, 100 mg, 150 mg, 200 mg, or more. In a preferred embodiment, hyaluronan can be provided in an amount sufficient to result in the administration of about 70 mg of hyaluronan (or hyaluronan extract) per day. Accordingly, certain embodiments (e.g., a daily dose) can include about 425 mg of (*Streptoccoccus* (equi subsp. *Zooepidemicus*)) hyaluronan (or sodium hyaluronate) (extract).

Hyaluronan can also be found in a wide variety of polymerization states and/or molecular weight (MW) sizes. Embodiments of the present disclosure can include so-called high molecular weight (HMW) hyaluronan, having a MW of greater than about 100 kDa, 200 kDa, 300 kDa, 400 kDa, 500 kDa, 600 kDa, 700 kDa, 800 kDa, 900 kDa, 1000 kDa, 1200 kDa, 1500 kDa, 1800 kDa, or more and/or less than about 3000 kDa, 3200 kDa, 3500 kDa, 3800 kDa, 4000 kDa, 4200 kDa, 4500 kDa, 4800 kDa, or 5000 kD. At least one embodiment can include hyaluronan having a MW of between about 100-5000 kDa, between about 500-4500 kDa, between about 1000-4000 kDa, between about 1200-3800 kDa, between about 1500-3500 kDa, or between about 1800-3000 kDa.

Fucoidan

Fucoidans are sulfated fucosylated (polysaccharide) polymers that exhibit some heparin/heparan sulfate-like properties, which are components of the glycocalyx matrix structure. Fucoidans have been isolated and studied for various biological activities, but have not been shown or recognized as contributing to glycocalyx repair (at sites of glycocalyx damage or perturbation), as contemplated by the present disclosure. Thus, although some benefits of fucoidan are known, it has not been previously known or contemplated that fucoidan can be introduced (exogenously) to repair damaged glycocalyx. Moreover, similar to hyaluronan, it is also unclear to what degree (orally) administered (exogenous) fucoidan can or does enter the circulatory system intact.

Indeed, fucoidan can be, act as, and/or provide a glycocalyx mimetic (or patch) that helps repair and maintain the backbone of the glycocalyx by (directly) associating with existing glycocalyx and/or glycocalyx-sparse regions of the endothelium. Thus, in addition to (naturally) produced heparin/heparan sulfate, which are synthesized and incorporated into the endothelium, exogenous or administered fucoidan can (directly) associate with existing glycocalyx and/or glycocalyx-sparse regions thereof. Introduction and/or administration of (exogenous) fucoidan causes thickening of endothelial glycocalyx at sites of damage and/or thinning of the glycocalyx. Certain fucoidans can also have antioxidant properties. Accordingly, introduction and/or administration of fucoidan can provide site-directed antioxidant activity at the endothelial glycocalyx and/or regions of the glycocalyx being repaired.

One or more embodiments of the present disclosure can include fucoidan (e.g., in an amount effective to increase the density of endothelial glycocalyx). In some embodiments the fucoidan can be included (or provided) as fucoidan sulfate. The fucoidan can be natural or synthetic. In a preferred embodiment, the fucoidan can be or comprise fucoidan (sulfate) extracted and/or purified from a (non-GMO) plant, preferably (brown, green, or red) seaweed or algae, more preferably *Laminaria*, such as *Laminaria japonica*. In at least one embodiment, the fucoidan (sulfate) (extract) can have a purity greater than or equal to about 75%, 80%, 85%, 90%, 92%, 95%, 96%, 97%, 98%, or 99%. Other genus and/or species of seaweed, including but not limited to *Monostroma*, such as *Monostroma nitidum*, are also contemplated herein.

The fucoidan can be included in compositions of the present disclosure in an amount of at least about 50 mg, 60 mg, 70 mg, 75 mg, 80 mg, 90 mg, 100 mg, 106.25 mg, 125 mg, 150 mg, 200 mg, 212.5 mg, 250 mg, 300 mg, 350 mg, 400 mg, 425 mg, 450 mg, 500 mg, 600 mg, 700 mg, 800 mg, 900 mg, 1000 mg, 1200 mg, or more. In a preferred embodiment, fucoidan can be provided in an amount sufficient to result in the administration of about 425 mg of fucoidan (or fucoidan extract) per day. Accordingly, certain embodiments (e.g., a daily dose) can include about 425 mg of (*Laminaria japonica*) fucoidan (sulfate) (extract).

3. Protecting Endothelial Glycocalyx—Antioxidants Superoxide Dismutase and Catalase Superoxide dismutase (SOD) (e.g., extracellular superoxide dismutase (ecSOD), or SOD3) and catalase are enzymes found in most living organisms exposed to oxygen, including animals, (green) plants, and most bacteria. SOD "dismutases" superoxide anions ($O_2^-$) to oxygen ($O_2$), or hydrogen peroxide ($H_2O_2$), which can be further decomposed (e.g., partially reduced) to hydroxyl radical ($HO^-$), or (fully reduced) to water ($H_2O$) and $O_2$ by catalase. Thus, SOD and catalase enzymes act as antioxidants capable of helping to prevent cellular and molecular damage caused by free radicals, such as reactive oxygen species/oxygen radicals, through "scavenging" the oxidants.

Glycocalyx can become damaged, perturbed, and/or destroyed by the action of oxidants, such as reactive oxygen species/oxygen radicals (e.g., $O_2^-$). Although supplemental forms of SOD and catalase have been reported to provide health benefits, there are no reports of either SOD or catalase having a potential impact on glycocalyx protection or defense, as contemplated by the present disclosure. Thus, although some benefits of SOD and catalase are known, it has not been previously recognized or contemplated that SOD and/or catalase can be introduced orally to protect or defend endothelial glycocalyx against (oxidative) damage (by free radicals). Moreover, it is also unclear to what degree (orally) administered (exogenous) SOD and catalase can or does enter the circulatory system intact.

Indeed, SOD and catalase can help protect and maintain the backbone of the endothelial glycocalyx. Reducing the degradation of glycocalyx constituents caused by excessive local levels of oxygen radicals can be one benefit of providing the anti-oxidant enzymes SOD and catalase, which bind to the glycocalyx and/or lower local concentrations of oxygen species, which in turn reduce oxidative damage to the glycocalyx and, thereby, preserve endothelial function.

For instance, exogenous, labeled SOD administered (orally and/or intravenously) to mice co-localizes (binds (directly) to) the endothelial glycocalyx. By so doing, the local concentration of SOD at the endothelial glycocalyx is increased, providing added or enhanced (site-directed) protection against oxygen radicals at the endothelial glycocalyx. Thus, in addition to (naturally) produced SOD, which may be synthesized and bound to the endothelium, exogenous or administered SOD can (directly) associate with (bind to) endothelial glycocalyx. Accordingly, introduction and/or administration of SOD can provide site-directed antioxidant activity at the endothelial glycocalyx.

Moreover, (oral and/or intravenous) administration of catalase to mice increases catalase concentrations in blood vessels. Thus, in addition to (naturally) produced SOD, which may be produced and secreted into the blood stream, exogenous or administered catalase can be absorbed into the blood stream and be available for oxidant scavenging at or adjacent to the endothelial glycocalyx (and SOD bound thereto). Accordingly, introduction and/or administration of catalase can also provide antioxidant activity in blood vessels and/or at the endothelial glycocalyx.

One or more embodiments of the present disclosure can include SOD (e.g., in an amount effective to increase scavenging of oxidants, such as free radicals, particularly reactive oxygen species/oxygen radicals (e.g., $O_2^-$) at or adjacent to the endothelial glycocalyx). In some embodiments the SOD can be included (or provided) as ecSOD, or SOD3, preferably bound to copper or zinc and/or as copper- or zinc-conjugated SOD. The SOD can be natural or synthetic. In a preferred embodiment, the SOD can be or comprise (ec)SOD (3) extracted and/or purified from (or be included as an extract of or from) a (non-GMO) plant (part), preferably one or more fruit or vegetable plant parts, more preferably *Momordica charantia* (a.k.a. bitter melon) (fruit). Other plant parts, including, for example, olive (fruit), artichoke (leaf), white grape (fruit), and/or red grape (fruit), are also contemplated herein.

One or more embodiments of the present disclosure can include catalase (e.g., in an amount effective to increase scavenging of oxidants, such as reactive oxygen species-/oxygen radical-precursors (e.g., $H_2O_2$), illustratively at or adjacent to the endothelial glycocalyx). In some embodiments the catalase can be included (or provided) bound to iron, such as iron(III) or iron(IV) and/or as iron(III)- or iron(IV)-conjugated catalase. The catalase can be natural or synthetic. In a preferred embodiment, the catalase can be extracted and/or purified from (or be included as an extract of or from) a (non-GMO) plant (part), preferably one or more fruit or vegetable plant parts, more preferably *Momordica charantia* (a.k.a. bitter melon) (fruit). Other plant parts, including, for example, olive (fruit), artichoke (leaf), white grape (fruit), and/or red grape (fruit), are also contemplated herein.

Antioxidants, such as SOD and/or catalase, can be included in compositions of the present disclosure (e.g., as *Momordica charantia* (a.k.a. bitter melon) (fruit) extract) in an amount of at least about 5 mg, 7.5 mg, 10 mg, 15 mg, 20 mg, 25 mg, 30 mg, 40 mg, 50 mg, 100 mg, 150 mg, 200 mg, or more. In a preferred embodiment, SOD and/or catalase can be provided in an amount sufficient to result in the administration of about 30 mg of SOD and/or catalase (or SOD and/or catalase extract) per day. Accordingly, certain embodiments (e.g., a daily dose) can include about 30 mg of ((bitter) melon (fruit)) antioxidant (e.g., SOD and/or catalase) (extract).

Other Naturally Occurring Antioxidants—Polyphenols

Antioxidants are potent scavengers of free radicals and other oxidants and serve as inhibitors of neoplastic processes and other cellular and/or molecular degrading, damaging, or destroying activities thereof. Naturally occurring antioxidants, widely available in fruits, vegetables, nuts, flowers and bark, possess a broad spectrum of biological and therapeutic properties against free radicals and oxidative stress. It has not, however, been shown that particular antioxidant compounds, such as polyphenols, can lower the concentration of oxygen radicals or other oxidants at or adjacent to the endothelial glycocalyx and/or and reduce oxidative damage thereto, as contemplated by the present disclosure. Thus, although some benefits of antioxidant compounds, such as polyphenols, are known, it has not been previously known or contemplated that such antioxidants can be introduced (exogenously) to protect and defend endothelial glycocalyx. Moreover, it is also unclear to what degree (orally) administered (exogenous) antioxidants, such as polyphenols, can or do enter the circulatory system intact.

Indeed, polyphenols can help protect and maintain the backbone of the endothelial glycocalyx by reducing the prevalence of oxidants in the blood stream. For instance, polyphenols extracted from olive, artichoke, and (white and/or red) grapes extracts can lower the concentration of oxygen radicals (e.g., in blood vessels) and thereby reduce damage of the glycocalyx.

In a preferred embodiment, antioxidants, such as polyphenols, can be extracted and/or purified from (or be included as an extract of or from) (non-GMO) plant(s), preferably (fruits and vegetables, including olive (fruit), artichoke (leaf), and white grape (fruit), and/or red grape (fruit). Antioxidants, such as polyphenols, can be included in compositions of the present disclosure in an amount of at least about 50 mg, 60 mg, 70 mg, 75 mg, 80 mg, 90 mg, 100 mg, 120 mg, 150 mg, 200 mg, 240 mg, 300 mg, 350 mg, 400 mg, 450 mg, 480 mg, 500 mg, 600 mg, 700 mg, 800 mg, 900 mg, 1000 mg, or more. In a preferred embodiment, polyphenols (e.g., derived and/or extracted from olive (fruit), artichoke (leaf), and white grape (fruit), and/or red grape (fruit)) can be provided in an amount sufficient to result in the administration of about 450 mg of (olive (fruit), artichoke (leaf), and white grape (fruit), and/or red grape (fruit)) polyphenol (extract) per day. Accordingly, certain embodiments (e.g., a daily dose) can include about 450 mg of (olive (fruit), artichoke (leaf), and white grape (fruit), and/or red grape (fruit)) polyphenol (extract).

In certain embodiments, (a mixture of (enzymatic and/or molecular)) antioxidants can be obtained as a (non-GMO) plant or plant-based extract. For instance, one or more fruit(s), vegetable(s), and/or other plant(s) or plant part(s) can be processed so as to extract, isolate, purify, and/or concentrate antioxidant(s), such as SOD, catalase, and/or polyphenol(s) therefrom. Extract(s) from a plurality of such plants or plant parts can be mixed together and/or included as an antioxidant component of (compositions of) the present disclosure. In at least one embodiment, for instance, the antioxidant mixture can comprise extracts, isolates, and/or concentrates of or from olive (fruit), artichoke (leaf), and white grape (fruit), red grape (fruit), and/or melon (fruit).

A mixture of (enzymatic and/or molecular) antioxidants, including, for example, SOD, catalase, and/or polyphenol(s) can be included in compositions of the present disclosure in an amount of at least about 50 mg, 60 mg, 70 mg, 75 mg, 80 mg, 90 mg, 100 mg, 120 mg, 150 mg, 200 mg, 240 mg, 300 mg, 350 mg, 400 mg, 450 mg, 480 mg, 500 mg, 600 mg, 700 mg, 800 mg, 900 mg, 1000 mg, or more. In a preferred embodiment, the antioxidant mixture can be provided in an amount sufficient to result in the administration of about 480 mg of the antioxidant (extract) mixture per day. Accordingly, certain embodiments (e.g., a daily dose) can include about 480 mg of (olive (fruit), artichoke (leaf), and white grape (fruit), red grape (fruit), and/or (bitter) melon (fruit)) polyphenol (extract).

Excipients and Non-Active Components

Various components (e.g., therapeutic agents or (active) ingredients) of the composition (as described above) may be combined with one or more excipients, such as microcrystalline cellulose and/or silicon dioxide, and then encapsulated using techniques known in the art. For example, the therapeutic agents may be combined with the excipients and dry blended. The resulting dry blend may then be encapsulated by hand or by machine. The microcrystalline cellulose and silicon dioxide act as excipients to allow the dry blend to flow smoothly into the capsules. Other known excipients may be added or substituted as necessary as determined by those having skill in the art. In addition, such excipients may be added in varying amounts without necessarily departing from the scope of this disclosure. The capsules may be any known in the art such as softgels, gelatin, and/or vegetarian capsules. The composition can also be provided as a tablet, pill, powder, dry blend, tincture, solution, suspension, (flavored or unflavored) drinks or drink mixes, aerosols, or other suitable form of matter.

In at least one embodiment, components of the present disclosure (e.g., therapeutic agents or (active) ingredients of the composition) can be coated and/or encapsulated to protect the therapeutic agents or (active) ingredients from degradation in the acidic conditions of the mammalian gut. For instance, in some embodiments, a protective coating can be formed around a dry blend of the components and the coated dry blended components optionally encapsulated (in a protective capsule) for oral administration. Alternatively, the coated dry blended components can be provide for and/or prepared as an oral slurry, solution, and/or suspension, such as a drink or tincture.

Example 1

An illustrative embodiment of (an encapsulated) composition of the present disclosure is provided in the table below:

| Composition of a 750.75 mg capsule | |
|---|---|
| Ingredient | Amount (mg/capsule) |
| Fucoidan (85%) | 106.25 mg |
| Antioxidants (SOD, catalase, polyphenols) | 120.00 mg |
| Glucosamine Sulfate | 375.00 mg |
| Hyaluronic Acid (1800-3000 kDa) | 17.50 mg |
| Microcrystalline Cellulose | 130.00 mg |
| Silicon Dioxide | 2.00 mg |
| Total mg per capsule | 750.75 mg |

The composition provided in Example 1 can be obtained commercially from MicroVascular Health Solutions, L.L.C., a Delaware limited-liability company, under the trademark ENDOCALYX™.

Embodiments of the present disclosure (e.g., one or more capsules having a composition of components according to Example 1) can be administered one or more times per day, and preferably up to four times per day. For example, four capsules can be administered once per day, two capsules can be administered two times per day, or one capsule can be administered four times per day. Alternatively, double-dose capsules comprising twice the above amounts can be provided. Such double-dose capsules can be provided, for example, as two capsules that can be administered one time per day or one capsule that can be administered two times per day. Other dosages, regimen, treatment (schedules), and/or formulations are also contemplated herein.

A preferred embodiment of the present disclosure comprises a daily dosage form of a composition comprising up to, at least, and/or about 1500 mg of glucosamine (e.g., glucosamine sulfate), 480 mg of a mixture of antioxidants (e.g., superoxide dismutase, catalase, and/or polyphenols), 425 mg of fucoidan (e.g., fucoidan sulfate), and 70 mg of hyaluronan (e.g., sodium hyaluronate). Such a daily dosage form can comprise a single dose, two one-half doses, three one-third doses, four one-fourth doses, and so forth. In addition, the dosage form can be provided as one, two, three, four, or more capsules, tablets, pills, or other dosage forms, such as a volume of liquid dose (e.g., drink), weight of a powdered or other dry dose (e.g., powdered drink mix), etc.

The embodiment described in Example 1 can represent a one-fourth daily dosage for a human or other (large) mammal. It will be appreciated, that dosage amounts of one or more (e.g., each) of the components (e.g., active ingredients and/or therapeutic agents) can be adjusted and/or modified, preferably while maintaining a similar ratio between such components. Accordingly, in at least one embodiment, a mammalian dosage form of the present disclosure can comprise a composition having a ratio of components according to the formula 375:120:106.25:17.50 (glucosamine (e.g., glucosamine sulfate):mixture of antioxidants (e.g., superoxide dismutase, catalase, and/or polyphenols): fucoidan (e.g., fucoidan sulfate):hyaluronan (e.g., sodium hyaluronate)), by weight, volume, or molar. Other ratios, for example, alternative ratios of up to about +/−1%, 2%, 5%, 10%, 15%, 20%, 25%, 30%, 35%, 40%, 45%, or 50% of one or more of the foregoing components (or ratios thereof) are also contemplated herein.

Synergistic Effects of Active Ingredients

As indicated herein, embodiments (e.g., compositions and/or methods) of the present disclosure can improve (micro)vascular health, not only through direct modes of action (as described above), but by exhibiting beneficial synergistic effects on endothelial glycocalyx (e.g., over the benefits of taking any single component (of the composition) alone or the sum of reported effects of the individual components. Complimentary or synergistic benefits of such components (or compositions (e.g., nutritional supplements) including the same) on the endothelial glycocalyx (and overall vascular health) include further enhancing the repair of glycocalyx damage, further stimulating synthesis of new glycocalyx (e.g., by enhancing production of glycocalyx precursors or building blocks), and/or further protecting glycocalyx (and constituents/components thereof) from (oxidative and/or other forms of degradation (e.g., enzymatic)).

Figure 4:
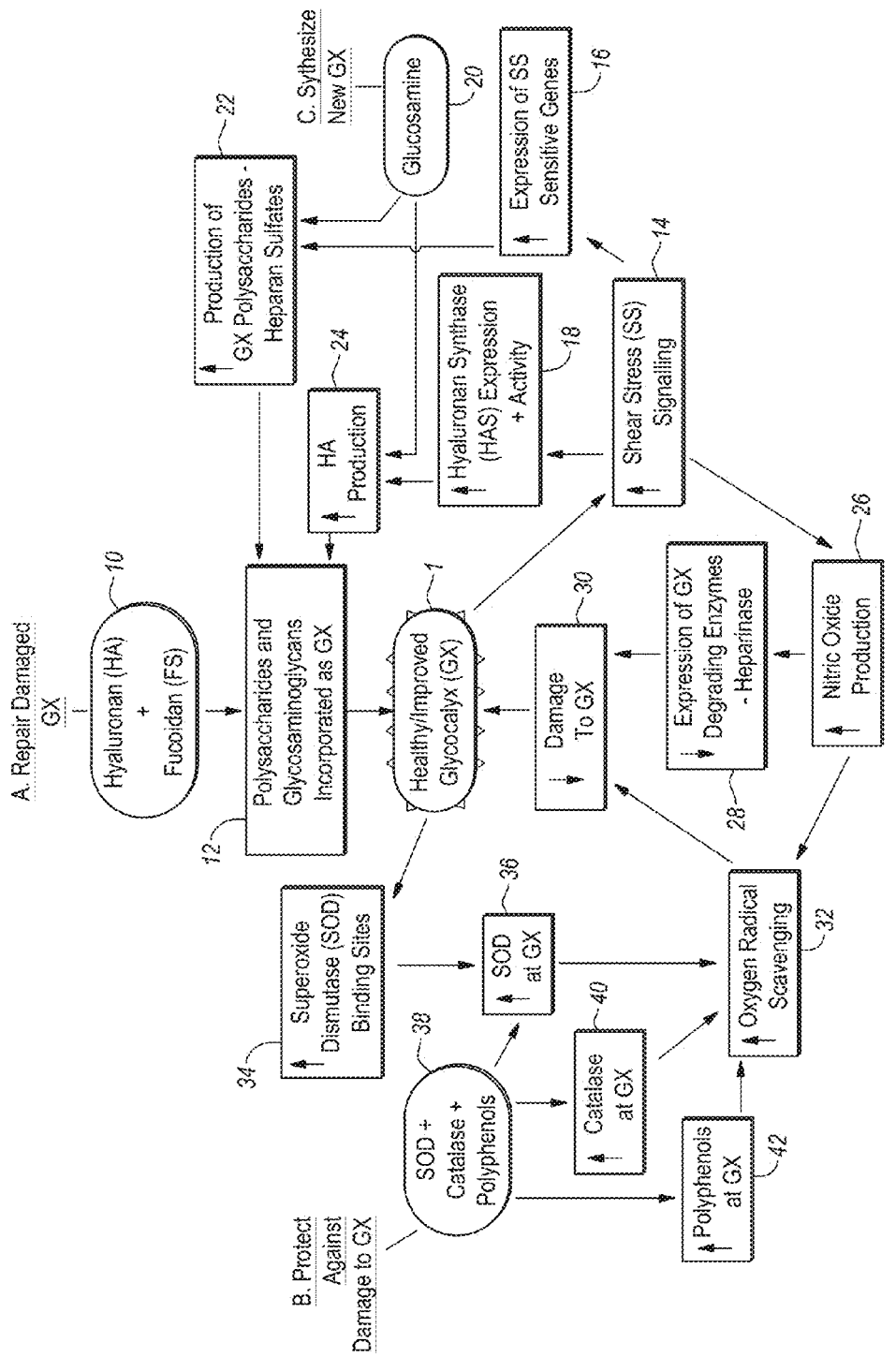
FIG. 4 illustrates a flowchart depicting synergistic interactions and effects of components of a synergistic glycocalyx treatment composition administered to a subject in need thereof in according to an embodiment of the present disclosure.

FIG. 4 is an illustrative synergistic flowchart illustrating one or more complimentary, synergistic, and/or overlapping modes of activity, leading to further enhanced or improved health of endothelial glycocalyx. As depicted in FIG. 4, a healthy and/or improved glycocalyx (GX) 1 can be achieved by three general, separate, distinct, overlapping, intersecting, and/or interrelated modes of action and/or activity, indicated as: A. repairing damaged GX; B. protecting against damage to GX; and C. synthesizing new GX.

As described herein, the addition and/or administration of one or more glycocalyx-mimetics 10, such as hyaluronan (HA) and/or fucoidan(s) (FS), can result in the (direct) incorporation 12 of such compounds (polysaccharides and/or glycosaminoglycans) at sites of GX damage and/or perturbation. Incorporation 12 can, therefore, repair (or patch) sites where the GX has been damaged, degraded, and/or destroyed, leading to healthy and/or improved GX 1. One consequence of healthy and/or improved GX 1 (e.g., from incorporation 12) can be an increase in the ability of the endothelium to function in shear stress (SS) signaling pathways 14. In particular, a healthy GX is associated with proper levels and/or modulation of SS signaling.

Proper and/or increased SS signaling 14 can result in a corresponding increase in the expression and/or activity of hyaluronan synthase (HAS) 18 and/or one or more (other) SS sensitive genes 16. The addition and/or administration of one or more GX precursors and/or building blocks 20, such as glucos amine, can feed one or more of activities 16 and/or 18, resulting, respectively, in an increase in the production of one or more GX polysaccharides 22, such as heparin sulfates, and/or increase production of one or more (non-sulfated) glycosaminoglycans 24, hyaluronic acid (HA). Increased production 22 and/or 24 can result in, correspond with, and/or be accompanied by incorporation 12 of such polysaccharides and/or glycosaminoglycans as new endothelial GX, further and/or synergistically improving, enhancing, and/or supporting healthy GX 1.

Proper and/or increased SS signaling 14 can also result in increased nitric oxide production 26. Increased nitric oxide production 26 can lead to decreased expression of one or more GX-degrading enzymes 28, such as heparinase, which can enzymatically digested and/or degrade heparin and/or heparin-like compounds (heparinoids), such as those described herein. Such degradation can cause (substantial and/or significant) damage to endothelial GX. Accordingly, decreased expression of GX degrading enzymes 28, such as heparinase, can cause and/or result in an (overall) decrease in endothelial GX damage 30, further and/or synergistically improving, enhancing, and/or supporting healthy GX 1.

Increased nitric oxide production 26 can also lead to improved and/or increased oxygen radical scavenging 32, which can further decrease endothelial GX damage 30, resulting in further and/or synergistically improved, enhanced, and/or healthy GX 1. Healthy and/or improved GX 1 also provides an increase in antioxidant (e.g., enzyme), such as superoxide dismutase (SOD), specifically, extracellular superoxide dismutase (ecSOD), or SOD3, binding sites 34. The addition and/or administration of one or more antioxidants 38, such as SOD, catalase, and/or polyphenols, can result in a corresponding increase in SOD at the GX 36, a corresponding increase in catalase at the GX 40 and/or a corresponding increase in polyphenols at the GX 42. One or more of increased antioxidants 36, 40, 42, can also result in improved and/or increased oxygen radical scavenging 32, which can further decrease endothelial GX damage 30, resulting in further and/or synergistically improved, enhanced, and/or healthy GX 1.

The increase in SOD at the GX 36 from the addition and/or administration of SOD at 38, in particular, coupled with the increase in antioxidant-binding sites 34 (e.g., for enzymes, such as SOD) provided by healthy and/or improved GX resulting from the addition and/or administration of one or more glycocalyx-mimetics 10, such as hyaluronan (HA) and/or fucoidan(s) (FS) and/or one or more GX precursors and/or building blocks 20, such as glucosamine, as described above, can enhance and/or increase oxygen radical scavenging 32, which can further decrease endothelial GX damage 30, resulting in further and/or synergistically improved, enhanced, and/or healthy GX 1. This healthy and/or improved GX 1 further enhances SS signaling 14, thereby enhancing nitric oxide production 26 and expression of relevant genes 16 and downstream products 18 and, coupled with the addition and/or administration of glucosamine 20 results in further production of GX constituents 22 and 24, which incorporate as GX 12, even further and/or synergistically improving, enhancing, and/or supporting healthy GX 1, which further protects against damage thereto, as described above.

Accordingly, embodiments of the present disclosure, including compositions comprising one or more components described herein, can produce synergistic (beneficial) outcomes, effects, and/or results on the structural and/or functional state and/or health of endothelial glycocalyx. Such components, while individually and/or directly impacting the health of endothelial glycocalyx through one of (A.) repairing damaged glycocalyx, (B.) protecting against damage to glycocalyx, or (C.) synthesizing new glycocalyx, can also synergistically enhance the health of endothelial glycocalyx by feeding, enhancing, or otherwise affecting one or more additional pathways and/or modes of action.

Specifically, inducing and/or effectuating repair (or patching) of damaged glycocalyx (e.g., through the addition and/or administration of one or more glycocalyx-mimetics, such as hyaluronan (HA) and/or fucoidan(s) (FS)), can also protect and/or defend against damage, degradation, and/or perturbation to the glycocalyx and/or increase (natural) synthesis of new glycocalyx. Similarly, protecting and/or defending against damage, degradation, and/or perturbation to the glycocalyx (e.g., through the addition and/or administration of one or more antioxidants, such as superoxide dismutase, catalase, and/or one or more polyphenols), can also enhance repair (or patching) of damaged glycocalyx and/or increase (natural) synthesis of new glycocalyx. Likewise, increasing (natural) synthesis of new glycocalyx (e.g., through the addition and/or administration of one or more glycocalyx precursors and/or building blocks, such as glucosamine), can also protect and/or defend against damage, degradation, and/or perturbation to the glycocalyx and/or enhance repair (or patching) of damaged glycocalyx.

Based on the foregoing description, the combined effect of certain, individual therapeutic agents or ingredients can be greater than the literature reported effects of each therapeutic agent or ingredient alone on glycocalyx repair, synthesis, and/or protection. Thus, although available literature shows an impact of the foregoing individual therapeutic agents on vascular and/or overall health, there is no report or suggestion of any one of them demonstrating an impact as an (exogenous and/or oral) supplement having an effect on glycocalyx repair and/or synthesis, let alone a synergistic effect.

Methods

A preferred method of administration comprises administering (to a patient or subject (e.g., a mammal, such as a human), in need thereof) an effective amount of one or more compositions described herein (e.g., in an acceptable pharmaceutical dose and/or dosage form, such as one, two, three, four, or more capsules, tablets, pills, etc., or a corresponding amount (e.g., by weight, volume, or molar) of powder, gel, granules, solution, suspension, tincture, etc.). Preferably, the compositions are administered orally, but the compositions may also be formulated for sublingual, rectal, vaginal, intravenous, subcutaneous, intramuscular, and transdermal administration as well. Thus, the compositions may be administered by various methods of delivery, such as but not limited to, conventional oral dosage forms, prepared drinks, (flavored or unflavored) drink mixes, aerosols, and intravenous drips. The compositions may be made using conventional techniques, such as by mixing the active agents with suitable excipients, such as but not limited to, binders, fillers, preservatives, disintegrators, flow regulators, plasticizers, dispersants, emulsifiers, etc. Suitable food-grade additives, such as but not limited to, sweeteners, colors, and flavoring agents may also be incorporated to encourage consumption.

Embodiments of the present disclosure are not limited to administration to humans, and may be administered to any animal, but are preferably administered to mammals. For example, one use aspect of the present disclosure comprises the administration of the compositions of the present disclosure to humans. While another use aspect of the present disclosure comprises the administration of the compositions of the present disclosure to mammals in the form of a veterinary composition that may be administered to bovines, equines, ovines, caprines, canines, felines, and other domestic animal species.

Thus, an embodiment of the present disclosure comprises administering a composition to a mammal comprising a (therapeutically-) effective amount of one or more of the components (e.g., active ingredients and/or therapeutic agents) described herein. For example, an oral dosage form of the compositions may be administered one or more times a day to achieve the desired physiological reaction or biological response.

As described in greater detail herein, each therapeutic agent is independently helpful for supporting and maintaining a healthy endothelial glycocalyx, thereby preserving or improving vascular health. For example, components such as glucosamine can be limiting reagents (precursor and/or building blocks) in a pathway for the synthesis of two main constituents of the endothelial glycocalyx—heparan sulfate and hyaluronan. Accordingly, the addition of available components such as glucosamine can enhance and support production of new glycocalyx, and can also support activities that protect and/or defend the glycocalyx against structural and/or functional damage, degradation, destruction, perturbation, etc. and/or repair (e.g., patch) endothelial glycocalyx at sites of glycocalyx damage, perturbation, etc.

Components such as hyaluronan and fucoidan can be and/or function as glycocalyx-mimetics that can repair (e.g., patch) endothelial glycocalyx at sites of glycocalyx damage, perturbation, etc. Accordingly, the addition of available components such as hyaluronan and fucoidan can repair damaged glycocalyx, and can also support activities that protect and/or defend the glycocalyx against structural and/or functional damage, degradation, destruction, perturbation, etc. and/or synthesize and incorporate new glycocalyx at the endothelium.

Component such as superoxide dismutase, catalase, and/or polyphenols can protect and/or defend endothelial glycocalyx against damage and/or degradation caused by enzymes and/or oxidants. Accordingly, the addition of components such as superoxide dismutase, catalase, and/or polyphenols can protect and/or defend endothelial glycocalyx against damage and/or degradation, and can also support activities that synthesize and incorporate new glycocalyx at the endothelium and/or repair (e.g., patch) endothelial glycocalyx at sites of glycocalyx damage, perturbation, etc.

Such components can be combined in any suitable manner or fashion, including various amounts (by weight, volume, or molar) and/or dosage forms to produce one or more compositions of the present disclosure. The compositions disclosed herein can be made into any dosage form and administered to a mammal, and more preferably to a human being. Preferably, an effective amount of one or more of the active agents can be mixed with appropriate excipients into the compositions disclosed herein and administered orally as an acceptable pharmaceutical dosage form, such as a capsule or tablet, though any suitable dosage form can be used in some embodiments. An oral dosage form of the compositions may be administered one or more times a day to achieve the desired physiological reaction or biological response. Optionally, the amount of each therapeutic agent or ingredient may be adjusted in each individual dosage form, and taken as needed to maintain the desired level of effectiveness.

Vascular health, particularly health of the endothelial glycocalyx, can be assessed via suitable detection or modulation of the endothelial glycocalyx. Methods of such detection and suitable biosensor devices are described in U.S. Pat. No. 8,759,095, the entirety of which is incorporated by reference herein. One suitable method of detection includes the use of the GLYCOCHECK® Microvascular Health Monitor available from MicroVascular Health Solutions, which is a complete imaging solution for screening a subject's or patient's perfused boundary region ("PBR") by accurately measuring and monitoring changes in the PBR in real time. The PBR in microvessels is the cell-poor layer which results from phase separation between the flowing red blood cells ("RBC") and plasma, and represents the most luminal part of the endothelial glycocalyx that allows cell penetration. Loss of endothelial glycocalyx integrity allows for deeper penetration by the outer edge of the RBC-perfused lumen, thereby increasing PBR, resulting in increased vulnerability of the endothelium.

PBR is thus a measure for the depth of penetration of red blood cells in the glycocalyx (or into the region where healthy glycocalyx should be found). Low values of PBR indicate a mechanically stable glycocalyx that protects the vessel wall against damage by circulating blood cells and other constituents, molecules or reagents circulating in the blood. The PBR is the main readout parameter calculated by the GLYCOCHECK® software. Calculation of further qualitative and/or quantitative (e.g., scores or numeric) measurements or representations can be performed manually or automatically (e.g., by the GLYCOCHECK® software). One such parameter—the Micro-Vascular Health Score (MVHS)—is discussed in further detail below.

The measurement may be performed non-invasively with a digital camera placed under the patient's tongue, underarm area, vagina, rectum, or other (highly) vascular area. It is noted that such measurements, while providing a local read of blood vessel structural features is highly indicative of an overall and/or systemic vascular landscape. For instance, measurements taken from one of the aforementioned locations can be confirmed (as accurate and representative of systemic vascular landscape) by measurement at other locations.

Other measurable indicators include (blood) volume, width and dimension of the glycocalyx, vessel density, the number of perfused vessels per tissue surface versus total number of vessels, RBC filling percentage, capillary volume reserve, enzyme activity, and presence or absence of glycocalyx contributing constituents, nitric oxide concentration in the blood, etc. Changes in any of the foregoing parameters, alone or in combination, are useful indicators for assessing vascular health.

Glycocalyx health may also be assessed via biological samples. For example, the status, volume or dimension of the glycocalyx and/or the activity of one or more enzymes of glycocalyx metabolism, may be performed via in vitro assays on a biological sample removed from a subject. Such in vitro assays are generally easy to perform and amenable to high-throughput analysis via techniques known in the art. Suitable samples include, but are not limited to, samples of whole blood, plasma or serum obtained from a subject. In vivo, such fluids directly contact the vascular endothelial tissue and are responsive to glycocalyx perturbation. Some glycocalyx indicators, for example glycocalyx associated lectin-like proteins, may also be detectable in urine.

Thus, profiles of lectin-like proteins that normally associate with the glycocalyx, as determined in the foregoing samples can provide suitable information about glycocalyx volume or dimension and/or molecular accessibility. Glycocalyx perturbation may also be diagnosed by detecting the presence and/or concentrations of glycocalyx derived molecules, such as but not limited to: oligo- or poly-saccharides, glycosaminoglycans, hyaluronan, heparan sulfate or proteoglycans; enzymes that catalyze glycocalyx anabolism or catabolism, such as hyaluronidase; and/or endogenous or exogenous substances that can become incorporated or otherwise associated with the glycocalyx.

More invasive techniques for assessing vascular health include invasive microscopic visualization techniques which comprise the injection of fluorescent labels attached to glycocalyx-bound proteins or glycocalyx permeating tracer molecules, and are contemplated herein.

As described above, the GLYCOCHECK® system can be used to measure PBR in subjects and/or patients. A PBR score can be calculated therefrom, providing an indication of the structural stability of the endothelial glycocalyx. In addition, (the in vivo camera of) the GLYCOCHECK® system can be used to measure capillary/blood vessel density in subjects and/or patients, providing an indication of overall number of capillary blood vessels that are visible (and red blood cell-perfused) in the captured region. A capillary red blood cell filling percentage can also be measured by the GLYCOCHECK® system in subjects and/or patients, providing an indication of the amount of red blood cells per blood vessel. Taken together, these indicators can be used to calculate a microvascular health score (MVHS) of the subjects and/or patients (e.g., population), which is directly proportional to blood vessel density, directly proportional to the capillary red blood cell filling percentage, and inversely proportional to PBR score.

The following results were obtained in a population of self-proclaimed "healthy" humans (with no known disease state or underlying health concerns) using the via GLYCOCHECK® system. A pretreatment baseline (BL) measurement was taken for each of the following vascular/glycocalyx health indicators: PBR; blood vessel density; and red blood cell filling percentage, and/or score(s) or measurements calculated therefrom. MVHS was also calculated from the foregoing indicators. The population averages of each indicator were normalized to 100% and plotted in FIG.

5 as a pretreatment baseline measurement of vascular/glycocalyx health (BL). The population was then orally administered a daily (4×) oral dosage of the composition described in Example 1 over a treatment course of 4 months, with the foregoing indicators measured and/or calculated after one, two, three, and four months, respectively. The (4×) dosage included about 1500 mg of glucosamine sulfate per day, about 425 mg of fucoidan sulfate per day, about 70 mg of sodium hyaluronate per day, and about 480 mg of a mixture of antioxidants (superoxide dismutase, catalase, and polyphenols), per day.

Figure 5:
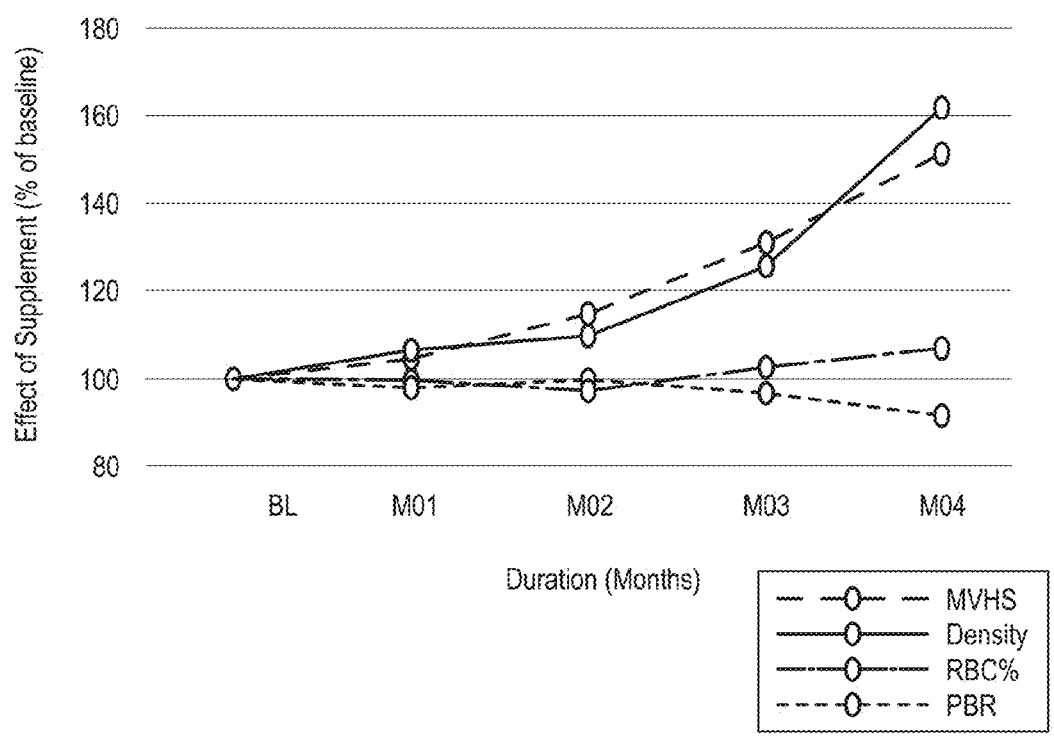
FIG. 5 illustrates the change in various endothelial glycocalyx health indicators in subject humans treated with a synergistic glycocalyx treatment composition according to an embodiment of the present disclosure.

As illustrated in FIG. 5, over the course of treatment, the population (on average) demonstrated an overall decrease in the PBR score (e.g., reflecting a more stable glycocalyx), an overall increase in the RBC filling percentage, indicating a per capita increase in the amount of red blood cells per blood vessel, and a significant increase in the number of capillaries visible and red blood cell-perfused. This blood vessel density increase can be seen as early as one month into the course of treatment and continues to improve month after month.

Accordingly, compositions of the present disclosure can substantially improve blood vessel density (i.e., the number of capillaries (e.g., perfused with red blood cells)), can increase the red blood cell filling percentage of such blood vessels, and can improve the stability of endothelial glycocalyx (as evidenced by a decrease in perfused boundary region). The MVHS based on these measurements and/or calculations improved substantially (e.g., by about 50%) over the course of treatment, beginning at the first month (e.g., about 5-10% improvement), to the second month (e.g., about 10-15% improvement), to the third month (e.g., about 30% improvement), and so forth. Accordingly, embodiments of the present disclosure can produce a substantial and/or significant (e.g., between about 5%-50%) improvement in microvascular health (over a one-month, two-month, three-month, and/or four-month treatment (comprising daily doses of the composition described in Example 1)).

These results indicate a surprising and unexpected improvement in the overall (micro)vascular health and specific indications described above following treatment with composition according to embodiments of the present disclosure.

It will also be appreciated that, based on the results presented in FIG. 10, further improvement in microvascular health is also contemplated herein. Indeed, because the microvascular health indicators have not plateaued by the fourth month of treatment, one of ordinary skill in the art would expect the level of such health indicators to continue improving over an additional course of treatment (e.g., five-months, six-months, seven-months, eight-months, nine-months, ten-months, eleven-months, twelve-months, or more).

The foregoing embodiments and examples are illustrative in nature and non-restrictive. The present disclosure may be embodied in other specific compositions without departing from the spirit, scope or attributes thereof. Thus, it will be readily apparent to those skilled in the art that modifications, derivations and improvements may be made without departing from the scope of the disclosure, and such modifications, derivations and improvements are intended to fall within the full scope and protection of the appended claims. Other equivalents to the specific embodiments disclosed herein may be recognizable to those skilled in the art and are also intended to fall within the full scope and protection of the appended claims.

In addition to the foregoing, patients or subjects treated with compositions of the present disclosure show a decrease in blood pressure and/or an increase in blood (plasma) nitric oxide levels, consistent with the proposed role of endothelial (micro(vascular)) glycocalyx and/or the flow chart depicted in FIG. 4.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, processes, and/or products according to certain embodiments of the present disclosure may include, incorporate, or otherwise comprise properties features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. It will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined.

Thus, disclosure of certain features relative to a specific embodiment of the present disclosure should not be construed as limiting application or inclusion of said features to the specific embodiment. Rather, it will be appreciated that other embodiments can also include said features without necessarily departing from the scope of the present disclosure. Moreover, unless a feature is described as requiring another feature in combination therewith, any feature herein may be combined with any other feature of a same or different embodiment disclosed herein. Furthermore, various well-known aspects of illustrative systems, processes, products, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. Each of the appended claims, as well as the recited elements thereof, is intended to be combinable with any other claim(s) and/or element(s) in any suitable combination or dependency without regard to the dependency in which said claims are presented. While certain embodiments and details have been included herein and in the attached disclosure for purposes of illustrating embodiments of the present disclosure, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

What is claimed is:

1. A method of treating endothelial glycocalyx, the method comprising administering to a mammal in need thereof a composition comprising:
   one or more molecular precursor of endothelial glycocalyx, comprising glucosamine, in an amount effective to increase production of endothelial glycocalyx;
   one or more antioxidant that associates with endothelial glycocalyx, comprising superoxide dismutase, in an amount effective to at least partially protect existing endothelial glycocalyx against damage caused by enzyme and/or oxidant; and
   one or more glycocalyx mimetic selected from the group consisting of a nonsulfated glycosaminoglycan, hyaluronan, a sulfated polysaccharide, and fucoidan, in an amount effective to increase the density of endothelial glycocalyx at a site of endothelial glycocalyx damage.

2. The method of claim 1, wherein administration of the composition exhibits a therapeutic effect on the endothelial glycocalyx of the mammal,
   the one or more molecular precursor enhancing synthesis of new glycocalyx, enhancing repair of damaged glycocalyx, and protecting existing glycocalyx against damage,
   the one or more antioxidant protecting existing glycocalyx against damage, enhancing synthesis of new glycocalyx, and enhancing repair of damaged glycocalyx, and
   the one or more glycocalyx mimetic enhancing repair of damaged glycocalyx, enhancing synthesis of new glycocalyx, and protecting existing glycocalyx against damage.

3. The method of claim 1, wherein the composition further comprises one or more additional antioxidants selected from the group consisting of:
   catalase or a suitable transition metal conjugate thereof, iron(III)-conjugated catalase, or iron(IV)-conjugated catalase; and
   one or more polyphenols.

4. The method of claim 1, wherein the composition comprises:
   hyaluronan, in the form of sodium hyaluronate or hyaluronic acid; and
   fucoidan, in the form of fucoidan sulfate.

5. The method of claim 4, wherein the glucosamine is in the form of non-GMO vegetable glucosamine sulfate, the hyaluronan is in the form of non-GMO microbial hyaluronic acid, and the fucoidan is in the form of non-GMO *Laminaria japonica* fucoidan sulfate.

6. The method of claim 4, wherein the composition further comprises one or more additional antioxidants, comprising:
   catalase or a suitable transition metal conjugate thereof, iron(III)-conjugated catalase, or iron(IV)-conjugated catalase; and
   a mixture of polyphenols.

7. The method of claim 6, wherein the glucosamine is include as glucosamine sulfate in an amount of at least about 375 mg, the fucoidan is included as fucoidan sulfate in an amount of at least about 106.25 mg, the hyaluronan is include as sodium hyaluronate in an amount of at least about 17.5 mg, and the antioxidants are included as a mixture of superoxide dismutase, catalase, and polyphenols in an amount of at least about 120 mg.

8. The method of claim 1, wherein administering comprises orally administering.

9. The method of claim 1, wherein the glucosamine is include as glucosamine sulfate in an amount of at least about 1500 mg, the fucoidan is included as fucoidan sulfate in an amount of at least about 425 mg, the hyaluronan is include as sodium hyaluronate in an amount of at least about 70 mg, and the antioxidants are included as superoxide dismutase, catalase, and a mixture of polyphenols in a total amount of at least about 480 mg.

10. The method of claim 1, wherein:
    the nonsulfated glycosaminoglycan comprises hyaluronan; and
    the sulfated polysaccharide comprises fucoidan.

11. The method of claim 10, wherein:
    the glucosamine is in the form of D-glucosamine, glucosamine sulfate, or a suitable salt of glucosamine;
    the superoxide dismutase is in the form of extracellular superoxide dismutase, SOD3, or a suitable transition metal conjugate of superoxide dismutase;
    the hyaluronan is in the form of sodium hyaluronate or hyaluronic acid; and
    the fucoidan is in the form of fucoidan sulfate.

12. The method of claim 1, wherein the composition comprises one or more nonsulfated glycosaminoglycans and one or more sulfated polysaccharides.

13. The method of claim 12, further comprising:
    catalase or a suitable transition metal conjugate thereof; and
    one or more polyphenols.

14. The method of claim 1, wherein administering comprises one or more sublingual, intravenous, subcutaneous, intramuscular, and transdermal administrations.

15. The method of claim 1, further comprising measuring integrity of the endothelial glycocalyx in the mammal, wherein measuring comprises obtaining imaging of microvascular of the mammal and calculating a microvascular health score for the mammal based on at least data derived from the imaging, the data including one or more indicators selected from the group consisting of capillary density, capillary red blood cell filling percentage, and perfused boundary region of the mammal.

16. The method of claim 15, further comprising diagnosing the mammal with a damaged or perturbed endothelial glycocalyx and prescribing a treatment protocol that includes administering the composition to the mammal.

17. A method of treating endothelial glycocalyx, the method comprising administering to a mammal in need thereof a composition comprising:
    one or more molecular precursor of endothelial glycocalyx, comprising glucosamine or a suitable salt thereof, in an amount effective to increase production of endothelial glycocalyx;
    one or more antioxidant that associates with endothelial glycocalyx, comprising superoxide dismutase or a suitable transition metal conjugate thereof, in an amount effective to at least partially protect existing endothelial glycocalyx against damage caused by enzyme and oxidant; and
    one or more glycocalyx mimetic selected from the group consisting of a hyaluronan or a suitable salt thereof and fucoidan or a suitable salt thereof, in an amount effective to increase the density of endothelial glycocalyx at a site of endothelial glycocalyx damage.

18. The method of claim 17, wherein the composition comprises hyaluronan or a suitable salt thereof and fucoidan or a suitable salt thereof.

19. The method of claim 18, wherein:
- the one or more molecular precursor of endothelial glycocalyx comprises glucosamine sulfate in an amount of at least about 375 mg;
- the one or more antioxidant comprises extracellular superoxide dismutase, catalase, and one or more polyphenols included in a total amount of at least about 120 mg; and
- the one or more glycocalyx mimetic comprises:
    - fucoidan sulfate in an amount of at least about 106.25 mg; and
    - sodium hyaluronate or hyaluronic acid in an amount of at least about 17.5 mg.

* * * * *